United States Patent [19]
Rao

[11] 4,197,286
[45] Apr. 8, 1980

[54] TESTOSTERONE DERIVATIVES AND ASSAY METHOD

[75] Inventor: Pemmaraju N. Rao, San Antonio, Tex.

[73] Assignee: Southwest Research Institute, San Antonio, Tex.

[21] Appl. No.: 837,269

[22] Filed: Sep. 27, 1977

[51] Int. Cl.$^2$ ............... G01N 33/16; A61K 43/00; C07D 471/00; C07J 41/00
[52] U.S. Cl. ................... 424/1; 260/112 B; 260/239.55 C; 260/397.1; 424/12
[58] Field of Search ............ 424/1, 12; 260/397.1, 260/112 B, 234.55 C

[56] References Cited
U.S. PATENT DOCUMENTS

| | | | |
|---|---|---|---|
| 4,031,117 | 6/1977 | Rao | 424/1 X |
| 4,085,202 | 4/1978 | Rao | 424/1 |

OTHER PUBLICATIONS

Ed. Gupta, Radio Immuno Assay of Steroid Hormones, Verlag Chemie, Weinheim, 1975, pp. 84–90.

*Primary Examiner*—Benjamin R. Padgett
*Assistant Examiner*—Christine M. Nucker
*Attorney, Agent, or Firm*—W. F. Hyer

[57] ABSTRACT

An anti-testosterone serum is provided which is highly selective to the measurement of testosterone using radioimmunossay techniques in both male and female plasma without resorting to chromatography even though the plasma may have a high 5α-dihydrotestosterone content. In addition, the high progesterone concentration normally present in female plasma has no effect on the assay of this plasma. The preferred hapten for producing the serum is 17β, 19-dihydroxyandrost-4-en-3-one 19-carboxymethyl ether although related compounds as disclosed herein are also useful.

22 Claims, No Drawings

TESTOSTERONE DERIVATIVES AND ASSAY METHOD

The invention described herein was made in the course of work under a grant or award from the Department of Health, Education, and Welfare.

The present invention relates to an anti-testosterone serum especially suited for use in the radioimmunoassay of testosterone and also to a steroid hapten and an immunogen for preparing such serum. The invention also relates to a method of radioimmunoassay using such serum, especially to one used without chromatography.

Since the initial demonstration by Furuyama et al (Steroids, 16, 415 [1970]) that testosterone can be accurately determined by a radioimmunoassay procedure, substantial efforts have been made to provide antisera which have a high degree of specificity to testosterone in the presence of other steroids which compete with testosterone in the reaction with the antisera. For a general discussion of these activities and the considerations involved, see the book entitled *Steroid Immunoassay*, edited by Cameron et al and published by Alpha Omega Publishing Ltd., Cardiff, Wales, U.K. (1975) and especially the material therein at pages 11–32. The primary aim of this work has been to develop haptens which ultimately could be used to provide the desired specific antisera. It has been desired that these antisera be sufficiently specific to avoid the necessity of resorting to chromatography to reduce the concentration of one or more competing steroids in the plasma sample being analyzed. For example, Rao et al discuss a highly specific antiserum for testosterone which can be used for measurement of testosterone in male plasma without chromatographic pre-treatment of the plasma sample (Steroids, 28, 101 [1976]). See also U.S. Pat. No. 4,031,117, issued June 21, 1977. As specifically discussed by Rao et al, their serum was generated from both rabbits and sheep immunized with 15β-carboxyethylmercaptotestosterone-BSA (bovine serum albumin) conjugate. While this serum could be used to assay the testosterone content of male plasma without chromatographic pre-treatment, it was not sufficiently selective to permit a similar analysis of female plasma. Thus this C-15 serum of Rao et al showed a cross-reactivity of over 2% with progesterone. As is well known, the latter appears in normal female serum in a concentration ranging from a substantial fraction of the testosterone concentration to a concentration which can be tenfold over that of testosterone. As a result, it has been the practice to treat female serum chromatographically to remove the progesterone before assaying the testosterone content.

It is accordingly an object of this invention to provide an anti-testosterone serum which is sufficiently specific to testosterone in the presence of significant quantities of progesterone to enable a radioimmunoassay assay to be made of a female serum without chromatographic pre-treatment thereof.

Another object is to provide such a serum which is likewise useable in the assay of male serum for testosterone.

Another object is to provide new testosterone derivatives useful to form conjugates capable of causing the production of such a serum.

In accordance with this invention the following testosterone derivatives can be used to prepare a conjugate and a serum to achieve the foregoing objects:

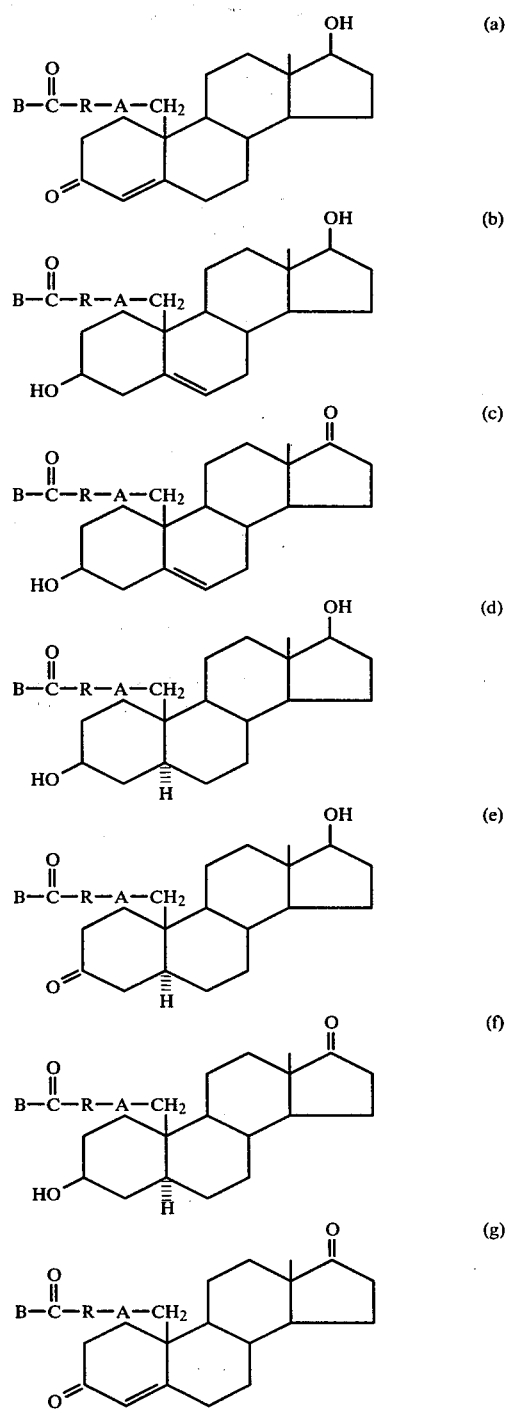

wherein
A is oxygen or sulfur;
R is an alkyl group of 1 to 10 carbon atoms; and
B is one of (i) —OH, —OM where M is an alkali metal or an alkaline earth metal, or (ii) —OY where Y is an alkyl group of 1 to 10 carbon atoms, or (iii) an amide having the formula

where P is an alkyl group of 1 to 10 carbon atoms or a substituted aryl group having the general formula

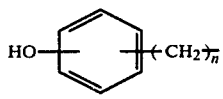

with n being from 1 to 10 or a substituted heterocyclic ring with one or more nitrogen atoms in the ring and having the general formula

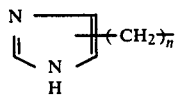

with n being from 1 to 10 and wherein the compounds are in the beta form.

A most preferred derivative is 17β, 19-dihydroxyandrost-4-en-3-one 19-carboxymethyl ether and the most preferred conjugate is such a derivative reacted with BSA.

When the derivatives are amides as above defined, the amide compound can be tagged with a suitable radioactive isotope, much as $^{125}$I, and the final product can be used as a radioactive tracer using techniques well known in the art, as, for example, those described in the above *Steroid Immunoassay* book. Preferred amines are histamine, tryamine and tyrosine methyl ester, with histamine being particularly preferred.

The following is one mode of synthesizing compound (a) above wherein A is oxygen, R is methyl group and B is a hydroxyl group:

Thus the first step is to protect the 19-hydroxyl group by reacting the 19-hydroxyandrost-4-en-3,17 dione (1) with dihydropyran. The resulting tetraphydropyranyl ether (2) is then reduced by the method Noremberski and Woods to the 17-hydroxyl form (3) following which the 17-hydroxyl is converted to an acetate by reaction with acetic anhydride to give (4). The tetrahydropyran ether is then hydrolyzed by reacting it with dilute acetic acid in tetrahydrofuran to produce the 19-hydroxyl compound (5). This is converted to the 19-carboxymethyl derivative by reaction with ethyldiazoacetate which was then hydrolyzed to the acid form (7).

EXAMPLE I

Androst-4-en-3,7-dione-19-(2'-tetrahydropyranyl)ether (2)

Freshly distilled dihydropyran (5 ml) was added dropwise over 3 minutes to a solution of 19-hydroxyandrost-4-ene-3,17-dione (5 g) and p-toluenesulfonic acid (250 mg) in anhydrous dioxane (50 ml). The reaction stirred for 3 additional minutes and then was brought to pH 8 with half-saturated methanolic ammonia. The dioxane was evaporated under vacuum and the reaction product was isolated with chloroform. The tetrahydropyranyl ether (2, 5.4 g, 82%) crystallized from ether-petroleum ether to give the analytical sample m.p. 140°-142°; $\nu_{Max}$ 1740, 1665, 1620 cm$^{-1}$; δ(CDCl$_3$): 0.92 (s, 18-CH$_3$), 3.57 and 4.16 (d, J=9 Hz, 19-CH$_2$), 4.61 (m, 2'-H), 5.93 (s, 4-H) ppm; MS, m/e=386 (M$^+$).

Anal. Calcd. for $C_{24}H_{34}O_4$: C, 74.58; H, 8.87. Found: C, 74.55; H, 8.95.

EXAMPLE II

17β-Acetoxyandrost-4-en-3-one-19-(2'-tetrahydropyranyl) ether (4)

A solution of diisobutylaluminum hydride in toluene (24.8%, 16.4 ml) was added through a rubber septum over 8 minutes to a stirred, cold (0° C.) solution of 2 (3.7 g) in toluene (80 ml). The reaction mixture was stirred under nitrogen at 0° for one hour then maintained at

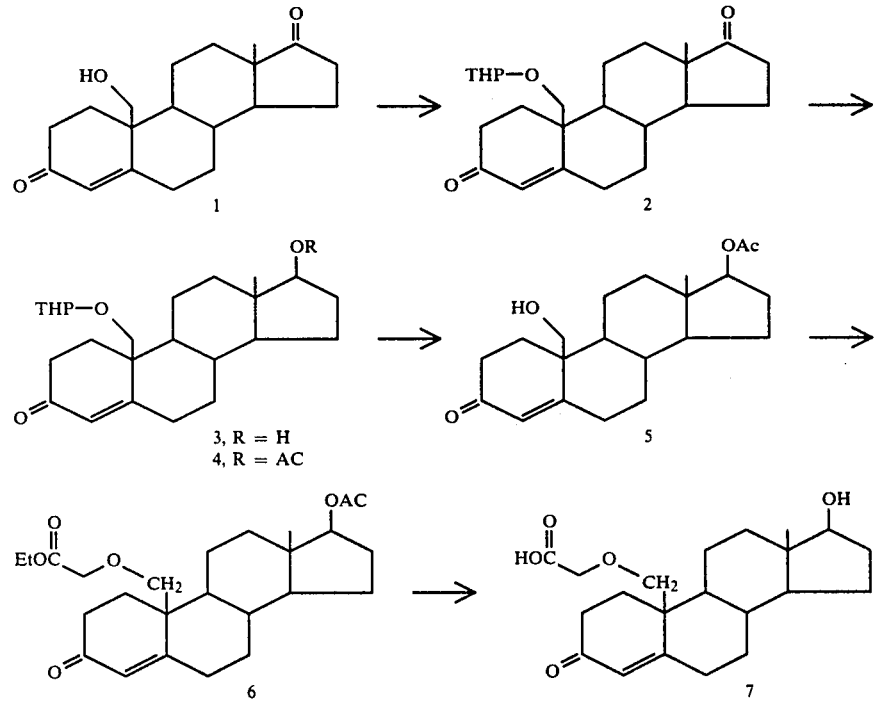

room temperature for one hour. After cooling to 0° C. once again, acetone (5.3 ml) and isopropanol (5.3 ml) were added slowly and then the reaction was stirred at room temperature for 14 hours. The reaction mixture was acidified with 1 N sulphuric acid and then immediately neutralized with solid sodium bicarbonate to prevent the hydrolysis of THP ether. The gelatinous precipitate of aluminium carbonate was filtered and the product was isolated from the filtrate with ethyl acetate. 17β-Hydroxyandrost-4-en-3-one-19-(2'-tetrahydropyranyl)ether (3, 5.6 g) was obtained as a gum and resisted crystallization. Its purity was established by thin layer chromatography. $\nu_{Max}$ 3440, 1668, 1622 cm$^{-1}$; δ(CDCl$_3$): 0.78 (s, 18-CH$_3$), 3.57 and 4.17 (d, J=9, 19-CH$_2$), 4.58 (m, 2'-H), 5.90 (s, 4-H) ppm.

The above 17β-hydroxy compound (3, 5.6 g) was dissolved in pyridine (35 ml) and acetic anhydride (35 ml) was added and the reaction mixture was left at room temperature in the dark for 18 hours. The reaction mixture was then evaporated under vacuum and the residue was purified on a dry silica gel column (32×790 mm) employing ether:ethyl acetate (8:2) as the developing solvent. The silica gel column, from 500–690 mm from origin, was cut and extracted with ethyl acetate to give pure tetrahydropyranyl ether 4 (2.29 g, 53%) which on crystallization from ether-petroleum ether melted at 128°–129° C. $\nu_{Max}$ 1740, 1675, 1625, 1250 cm$^{-1}$; δ(CDCl$_3$): 0.83 (s, 18-CH$_3$), 2.02 (s, 17-OAc), 3.55 and 4.14 (d, J=9, 19-CH$_2$), 4.61 (m 2'-H and 17-H), 5.80 (s, 4-H)ppm; MS, m/e=430 (M+).

Anal. Calcd. for C$_{26}$H$_{38}$O$_5$: C, 72.53; H, 8.90. Found: C, 72.49; H, 8.98.

EXAMPLE III

17β,19-Dihydroxyandrost-4-en-3-one 17-acetate (5)

The THP ether 4 (2.3 g) was dissolved in a mixture of acetic acid (45 ml), water (15 ml), and tetrahydrofuran (15 ml) and stirred at 70° for 3 hours. The reaction mixture was then cooled and evaporated to dryness under reduced pressure. The product so obtained was combined with the residue obtained by similar hydrolysis of 4 (0.3 g) from an earlier batch. The amount from both batches was combined and crystallized from dichloromethane-ether to give 5 (1.57 g) m.p. 166°–168° C.; $\nu_{Max}$ 3350, 1745, 1667, 1620, 1240 cm$^{-1}$; $\nu_{Max}$ 243 nm (ε=15,116) (MeOH); δ(CDCl$_3$) 0.82 (s, 18-CH$_3$), 2.02 (s, 17-OAc), 3.91 and 4.10 (d, J=10.5 Hz, 19-CH$_2$), 4.65 (m, 17-H), 5.95 (s, 4-H) ppm; Ms, m/e=346 (M+)

Anal. Calcd. for C$_{21}$H$_{30}$O$_4$: C, 72.80; H, 8.73. Found: C, 72.92; H, 9.04.

EXAMPLE IV

17β,19-Dihydroxyandrost-4-en-3-one 19-carboxymethylether (7)

To a solution of the 19-alcohol 5 (200 mg) and rhodium (II) acetate dimer (2 mg) in benzene (8 ml), ethyldiazoacetate (2 ml) in benzene (3 ml) was added dropwise over a period of 40 minutes. The mixture was then stirred at room temperature for 16 hours. The rhodium catalyst was removed from the solution by filtration through silica gel. The silica gel was washed with ethyl acetate and the organic solvent evaporated to give the desired product contaminated with unreacted starting material. Another 200 mg batch was processed similarly and the product obtained from the two batches was purified on a dry silica gel column (15×1090 mm) employing ether as the developing solvent. The silica gel column, from 745–870 mm from the origin, was cut and extracted with ethyl acetate to give 80 mg of the ethyl ester 6 as an oil (16%). $\nu_{Max}$ 1738, 1665, 1623, and 1250 cm$^{-1}$; δ(CDCl$_3$): 0.84 (s, 18-CH$_3$),

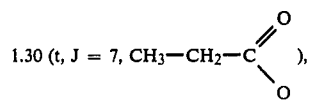
1.30 (t, J = 7, CH$_3$—CH$_2$—C(=O)—O—), 2.00 (s, 17-acetate), 3.73 and 3.95 (d, J=9 Hz, 19-CH$_2$),

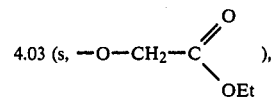
4.03 (s, —O—CH$_2$—C(=O)—OEt), 4.20 (q, J=7, -O-CH$_2$-CH$_3$), 4.63 (m, 17-H), 5.90 (s, 4-H) ppm.

The 19-ether (6, 132 mg) obtained from different batches was dissolved in anhydrous methanol (10 ml) and sodium methoxide (200 mg) was added and stirred at room temperature under nitrogen. After 45 minutes the methanol was evaporated under nitrogen and the residue was diluted with water. Unhydrolyzed material was removed by extraction with methylene chloride. The combined aqueous extracts were cooled in an ice bath, then acidified to pH 2 with conc. HCl. The acid 7 was isolated with methylene chloride and crystallized from methylene chloride-ether (41 mg, 37%), m.p. 190°–192° C.; $\nu_{Max}$ 3430, 1740, 1655 cm$^{-1}$; $\lambda_{Max}$ 242 (ε=13,449); δ(CD$_3$OD) 0.78 (s, 18-CH$_3$), 3.57 (m, 17-H), 3.80 and 4.02 (d, J=9, 19-CH$_2$),

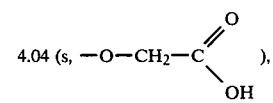
4.04 (s, —O—CH$_2$—C(=O)—OH), 5.84 (s, 4-H) ppm; MS, m/e=362 (M+)

Anal. Calcd. for C$_{21}$H$_{30}$O$_5$: C, 69.59; H, 8.34. Found: C, 69.40; H, 8.26.

The haptens of this invention are capable, when linked to a suitable immunological carrier, preferably a protein, to produce a conjugate which can be employed in a host animal to elicit anti-testosterone serum specific to testosterone even in the presence of 5ε-dihydrotestosterone and progesterone. As used in this specification the term "immunological carrier" means a conjugate as described herein capable of causing an immunological response in a host animal. Among such carriers are proteins, polymers, polysaccharides and polypeptides, all of which should have a molecular weight of over 1000. The preferred carrier is bovine serum albumin (BSA); and other examples are the globulins, alpha, beta and thyro; poly (L-Lysine) and the like.

The conjugation of the instant haptens to the carrier can be by procedures which per se are well known to those skilled in the art. A coupling agent such as mixed anhydrides, can be used.

Likewise, the procedures for injecting the conjugate into a host animal and the recovery of the anti-body are well known.

EXAMPLE V

17β, 19-dihydroxyandrost-4-en-3-one 19-carboxymethyl ether conjugated with BSA at a concentration of 2 mg/ml was emulsified with an equal volume of isotonic saline solution and Freund's adjuvaant (1:1) and used for the immunization of rabbits. Four female New Zealand rabbits were employed and the anti-sera collected and evaluated. The latter included determining the cross-reactivity of 5α-dihydrotestosterone. The cross-reactivity found was as follows:

TABLE 1

| RABBIT NO. | % CROSS-REACTION |
|---|---|
| X-181 | 5.80 |
| X-182 | 18.79 |
| X-183 | 17.80 |
| X-184 | 34.20 |

From this data, it is apparent that the anti-testosterone serum from rabbit No. X-181 exhibited low cross-reactivity with 5α-dihydrotestoserone. The serum from this rabbit was used in the further experiments reported herein.

This particular antiserum showed a titer of 1:175,000 in binding 50% of 50 pg of tritiated testosterone.

Also, the cross-reactivity of pertinent and structurally similar steroids was determined to be as follows:

TABLE 2

| STERIOD | % CROSS-REACTIVITY |
|---|---|
| 1. Testosterone | 100.00 |
| 2. 5α-Dihydrotestosterone | 6.65 |
| 3. 11β-Hydroxytestosterone | 0.00 |
| 4. 11β-Oxotestosterone | 1.80 |
| 5. 11β-Hydroxyandrostenodione | 0.00 |
| 6. Androstenedione | 0.90 |
| 7. 5β-Androstane-3,17-dione | 0.00 |
| 8. 5β-Androstane-3,17-dione | 0.00 |
| 9. 5β-Dihydrotestosterone | 0.63 |
| 10. Androsterone | 0.00 |
| 11. Epiandrosterone | 0.19 |
| 12. 5α-Androstane-3α, 17β-diol | 0.00 |
| 13. 5α-Androstane-3β,17β-diol | 2.19 |
| 14. 5-Androstene-3β,17β-diol | 0.51 |
| 15. Dehydroepiandrosterone | 0.00 |
| 16. 6α-Hydroxytestosterone | 0.75 |
| 17. Estrone | 0.00 |
| 18. Estradiol | 0.43 |
| 19. Estriol | 0.00 |
| 20. Progesterone | 0.00 |
| 21. Corticosterone | 0.00 |
| 22. Deoxycorticosterone | 0.00 |

The binding affinity constant of this antiserum is $K_a = 6.15 \times 10^9$ liters/mole.

As indicated above, the antiserum of this invention can be used to determine the testosterone content of both male and female plasma without resorting to chromatographic pre-treatment. Tables 3 and 4 show comparative analyses of pooled male and female sera each with and without chromatographic pre-treatment and employing the anti-serum of Rabbit X-181:

TABLE 3

| | MALE PLASMA | | |
|---|---|---|---|
| TYPE OF MEASUREMENT | TESTOSTERONE MEASURED (Ng %) | COEFFICIENT OF VARIATION (%) | NO. OF SAMPLES |
| Extraction Only | 576.1 | 6.6 | 16 |
| LH-20 Chromatography | 576.8 | 3.4 | 16 |

TABLE 4

| | FEMALE PLASMA | | |
|---|---|---|---|
| TYPE OF MEASUREMENT | TESTOSTERONE MEASURED (Mg %) | COEFFICIENT OF VARIATION (%) | NO. OF SAMPLES |
| Extraction Only | 26.2 | 3.9 | 8 |
| LH-20 Chromatography | 23.7 | 7.1 | 8 |

The antiserum was further evaluated by measuring plasma testosterone levels in a normal female for two menstrual cycles as indicated in Table 5. The assays were performed on plasma samples after direct extraction with ether:chloroform (4:1) and the extracts were not subjected to chromatographic purification. These results were then compared with data obtained on the same samples employing the anti-testosterone-C-15 serum of Rao et al as above identified after subjecting the extracts to thin layer chromatography (TLC). The results of these investigations are presented in Table 5.

TABLE 5

| CYCLE | CYCLE DAY | ANTI-TESTOSTERONE C-15 SERUM WITH TLC (Ng %) | ANTI-TESTOSTERONE C-19 SERUM WITHOUT TLC (Ng %) | PROGESTERONE (Ng %) |
|---|---|---|---|---|
| I | 9 | 37.9 | 37.5 | 13.3 |
| | 10 | 155.5* | 32.3 | 19.6 |
| | 11 | 118.2* | 33.0 | 20.3 |
| | 12 | 30.6 | 34.8 | 34.7 |
| | 13 (ovulation) | 45.2 | 35.2 | 94.2 |
| | 14 | 22.6 | 22.4 | 126.8 |
| | 15 | 40.5 | 32.6 | 250.5 |
| | 16 | 38.6 | 29.2 | 323.6 |
| | 17 | 43.3 | 29.7 | 304.1 |
| | 20 | 74.6 | 23.2 | 472.0 |
| | 23 | 40.7 | 25.8 | 305.2 |
| | 27 (menses) | 34.1 | 26.1 | 43.2 |
| II | 7 | 79.0 | 33.2 | 12.1 |
| | 9 | 64.2 | 37.8 | 17.2 |
| | 11 (ovulation) | 47.8 | 42.3 | 69.9 |
| | 15 | 157.2* | 28.0 | 228.5 |
| | 18 | 55.8 | 26.6 | 647.1 |
| | 21 | 44.1 | 24.8 | 510.9 |
| | 25 | 86.4 | 30.4 | 270.2 |

*Unexplainable higher values obtained on chromatographic samples.

The invention having been described, what is claimed is:

1. A compound selected from the group consisting of:

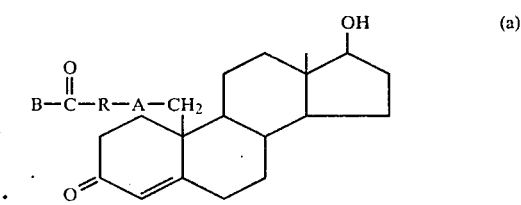

(a)

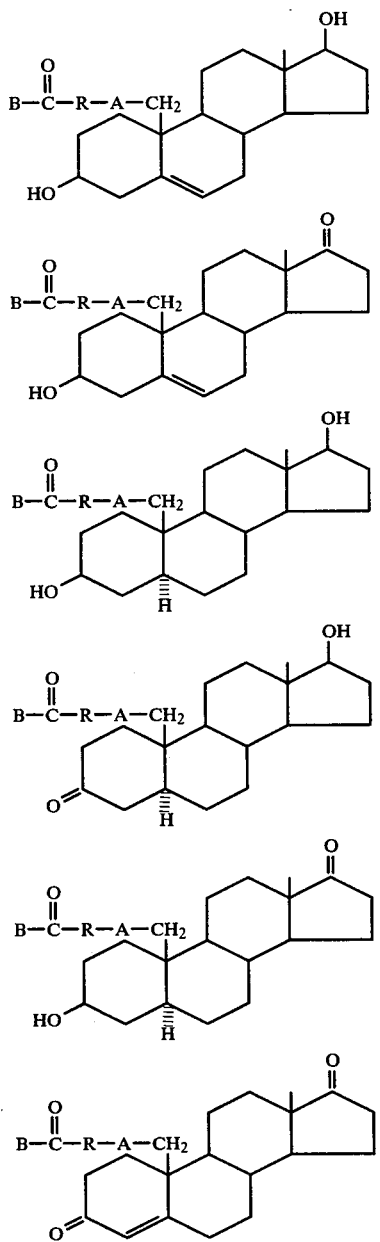

wherein

A is oxygen or sulfur;

R is an alkyl group of 1 to 10 carbon atoms; and

B is one of (i) —OH, —OM where M is an alkali metal or an alkaline earth metal, or (ii) —OY where Y is an alkyl group of 1 to 10 carbon atoms, or (iii) an amide having the formula

where P is an alkyl group of 1 to 10 carbon atoms or a substituted aryl group having the general formula

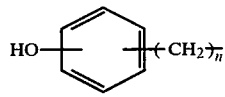

with n being from 1 to 10 or a substituted heterocyclic ring with one or more nitrogen atoms in the ring and having the general formula

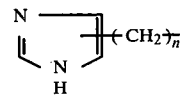

with n being from 1 to 10 and wherein the compounds are in the beta form.

2. The compound of claim 1 wherein A is oxygen.

3. The compound of claim 1 wherein R has one carbon atom.

4. The compound of claim 1 wherein B is —OH.

5. 17β, 19-dihydroxyandrost-4-en-3-one 19-carboxymethyl ether.

6. An immunogen comprising a compound of claim 1 conjugated to an immunological carrier.

7. An immunogen comprising a compound of claim 2 conjugated to an immunological carrier.

8. An immunogen comprising a compound of claim 3 conjugated to an immunological carrier.

9. An immunogen comprising a compound of claim 4 conjugated to an immunological carrier.

10. An immunogen comprising a compound of claim 5 conjugated to an immunological carrier.

11. The immunogen of claim 5 wherein the carrier is bovine serum albumin (BSA).

12. The antibody produced by injecting an immunogen of claim 6 into a host animal.

13. The antibody produced by injecting an immunogen of claim 7 into a host animal.

14. The antibody produced by injecting an immunogen of claim 8 into a host animal.

15. The antibody produced by injecting an immunogen of claim 9 into a host animal.

16. The antibody produced by injecting an immunogen of claim 10 into a host animal.

17. The antibody produced by injecting an immunogen of claim 11 into a host animal.

18. A method of making a radioimmunoassay of testosterone in a sample employing radiolabeled testosterone and an antibody, characterized by employing an antibody produced by injecting, into a host animal, a conjugate of 17β, 19-dihydroxyandrost-4-en-3-one 19-carboxymethyl ether and bovine serum albumin (BSA).

19. The method of claim 18 wherein the ether is thioether.

20. The method of claim 18 wherein the sample is prepared without chromatographic separation.

21. The method of making a radioimmunoassay of testosterone in a sample obtained from a female during her menstrual cycle so that the sample contains a relatively high content of progesterone as compared to the testosterone content comprising the step of conducting said assay using an antibody produced by injecting into a host animal, a conjugate of 17β, 19-dihydroxyandrost-4-en-3-one 19-carboxymethyl ether and bovine serum alubmin (BSA).

22. The method of claim 21 wherein the sample is prepared without chromatographic separation.

* * * * *

UNITED STATES PATENT AND TRADEMARK OFFICE
CERTIFICATE OF CORRECTION

PATENT NO. : 4,197,286
DATED : April 8, 1980
INVENTOR(S) : Pemmaraju Narasimha Rao It is certified that error appears in the above—identified patent and that said Letters Patent is hereby corrected as shown below:

On the title page the assignee, should read:

-- Southwest Foundation For Research And Education --.

Signed and Sealed this

Third Day of February 1981

[SEAL]

Attest:

RENE D. TEGTMEYER

Attesting Officer

Acting Commissioner of Patents and Trademarks